United States Patent
Wines et al.

(10) Patent No.: US 12,097,142 B2
(45) Date of Patent: Sep. 24, 2024

(54) OSTOMY APPLIANCE WITH CUSTOMIZABLE BARRIER RING FOR LOCALIZED CONVEX SUPPORT

(71) Applicant: Hollister Incorporated, Libertyville, IL (US)

(72) Inventors: James P. Wines, Algonquin, IL (US); Ryan S. Park, Northbrook, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 0 days.

(21) Appl. No.: 18/553,030

(22) PCT Filed: Apr. 25, 2023

(86) PCT No.: PCT/US2023/066162
§ 371 (c)(1),
(2) Date: Sep. 28, 2023

(87) PCT Pub. No.: WO2024/050157
PCT Pub. Date: Mar. 7, 2024

(65) Prior Publication Data
US 2024/0268988 A1    Aug. 15, 2024

Related U.S. Application Data

(60) Provisional application No. 63/403,129, filed on Sep. 1, 2022.

(51) Int. Cl.
*A61F 5/448* (2006.01)
*A61F 5/44* (2006.01)
*A61F 5/445* (2006.01)

(52) U.S. Cl.
CPC ...... *A61F 5/448* (2013.01); *A61F 2005/4483* (2013.01)

(58) Field of Classification Search
CPC .............. A61F 5/448; A61F 2005/4483; A61F 5/445
See application file for complete search history.

(56) References Cited

U.S. PATENT DOCUMENTS 4,219,023 A     8/1980  Galindo
4,419,100 A  * 12/1983  Alexander .............. A61F 5/448
                                                        604/339

(Continued)

FOREIGN PATENT DOCUMENTS

EP        0381393 A1     8/1990
EP        0812583 A1  *  6/1997  ............. A61F 5/448

(Continued)

OTHER PUBLICATIONS

International Search Report issued by ISA/EPO in connection with PCT/US2023/066162 dated Jun. 20, 2023.

(Continued)

*Primary Examiner* — Guy K Townsend
(74) *Attorney, Agent, or Firm* — Klintworth & Rozenblat IP LLP

(57) ABSTRACT

An ostomy appliance that comprises a convex ring insert member. The insert member can have a curved body-side surface, an opposing pouch-side surface defining an internal cavity and an annular curved body portion between an outside flange and an engagement portion encircling a centrally-located input opening. The engagement portion can comprise a plurality of spaced-apart flexible tabs. The internal cavity can be defined by interior surfaces of the flexible tabs and the curved body portion. The flexible tabs can have flexibility to bend toward the internal cavity. A backfill material can be applied into the internal cavity along the interior surfaces of at least some of the flexible tabs. The backfill material can be removable from the ring insert. Upon application of the backfill material, the flexibility of (Continued)

some of the flexible tabs can be reduced to provide a localized rigid support segment along the engagement portion.

20 Claims, 5 Drawing Sheets

(56) References Cited

U.S. PATENT DOCUMENTS

| | | | |
|---|---|---|---|
| 4,592,750 A | 6/1986 | Kay | |
| 4,610,676 A * | 9/1986 | Schneider | A61F 5/448 604/339 |
| 5,163,930 A * | 11/1992 | Blum | A61F 5/448 604/338 |
| 5,330,454 A * | 7/1994 | Klingler | A61F 5/448 604/338 |
| 5,370,692 A | 12/1994 | Fink | |
| 5,501,677 A * | 3/1996 | Jensen | A61F 5/448 604/338 |
| 5,607,413 A * | 3/1997 | Holmberg | A61F 5/448 604/338 |
| 5,730,735 A * | 3/1998 | Holmberg | A61F 5/448 604/338 |
| 6,093,276 A * | 7/2000 | Leise, Jr. | A61F 5/448 604/338 |
| 6,589,222 B1 * | 7/2003 | Olsen | A61F 5/449 604/336 |
| 6,673,056 B2 * | 1/2004 | Metz | A61F 5/448 604/338 |
| 6,740,067 B2 * | 5/2004 | Leise, Jr. | A61F 5/448 604/336 |
| 6,863,663 B1 * | 3/2005 | Mills | A61F 5/443 604/337 |
| 7,029,464 B2 * | 4/2006 | Fenton | A61F 5/448 604/277 |
| 7,258,661 B2 | 8/2007 | Davies | |
| 8,211,073 B2 * | 7/2012 | Dove | A61F 5/445 604/338 |
| 9,149,265 B2 | 10/2015 | Ehrenreich | |
| 9,517,157 B2 * | 12/2016 | Hanuka | A61F 5/4407 |
| 9,770,359 B2 | 9/2017 | Edvardsen | |
| 9,928,341 B2 | 3/2018 | Angelides | |
| 9,999,537 B2 | 6/2018 | Ekfeldt | |
| 10,512,562 B2 | 12/2019 | Kavanagh | |
| 10,531,977 B2 | 1/2020 | Schoess | |
| 10,893,974 B2 | 1/2021 | Nyberg | |
| 11,246,739 B2 * | 2/2022 | Ekfeldt | A61F 5/443 |
| 11,484,432 B2 * | 11/2022 | Hansen | A61F 5/4404 |
| 11,571,325 B2 * | 2/2023 | Kavanagh | A61F 5/448 |
| 2004/0106908 A1 * | 6/2004 | Leise, Jr. | A61F 5/448 604/355 |
| 2004/0193122 A1 * | 9/2004 | Cline | A61F 5/445 604/332 |
| 2012/0059341 A1 * | 3/2012 | Masters | A61F 5/448 604/339 |
| 2014/0148771 A1 * | 5/2014 | Luce | A61F 5/448 604/345 |
| 2014/0316360 A1 | 10/2014 | Ekfeldt | |
| 2015/0359656 A1 * | 12/2015 | Hansen | A61F 5/443 604/344 |
| 2019/0083295 A1 * | 3/2019 | Cisko, Jr. | A61F 5/449 |
| 2019/0231580 A1 * | 8/2019 | Czaplewski | A61F 5/448 |
| 2019/0254864 A1 * | 8/2019 | Czaplewski | A61F 5/443 |
| 2020/0253777 A1 * | 8/2020 | Jones | A61F 5/443 |
| 2020/0281758 A1 | 9/2020 | Tan | |
| 2020/0337884 A1 * | 10/2020 | Donovan | A61F 5/448 |
| 2021/0307952 A1 * | 10/2021 | Nielsen | A61F 5/448 |

FOREIGN PATENT DOCUMENTS

| | | |
|---|---|---|
| EP | 0800804 A1 | 10/1997 |
| EP | 1275357 A2 | 1/2003 |
| EP | 1348412 A1 | 10/2003 |
| EP | 2298251 A2 | 3/2011 |
| EP | 2497449 A2 | 9/2012 |
| EP | 2651351 B1 | 5/2015 |
| EP | 2370030 B1 | 8/2015 |
| EP | 2482767 B1 | 12/2015 |
| EP | 1485048 B1 | 6/2016 |
| EP | 3175830 A1 | 6/2017 |
| EP | 3178452 A1 | 6/2017 |
| EP | 2950761 B1 | 8/2017 |
| EP | 3238671 A1 | 11/2017 |
| EP | 2558043 B1 | 10/2018 |
| EP | 3270835 B1 | 5/2019 |
| EP | 3488888 A1 | 5/2019 |
| EP | 3727246 A1 | 10/2020 |
| EP | 3897481 B1 | 8/2023 |
| WO | 9930653 A1 | 6/1999 |
| WO | 2015132779 A1 | 9/2015 |
| WO | 2020200382 A1 | 10/2020 |
| WO | 2020220025 A1 | 10/2020 |
| WO | 2021037321 A1 | 3/2021 |

OTHER PUBLICATIONS

Written Opinion issued by ISA/EPO in connection with PCT/US2023/066162 dated Jun. 20, 2023.
International Search Report issued by ISA/EPO in connection with PCT/US2023/066160 dated Jul. 14, 2023.
Written Opinion issued by ISA/EPO in connection with PCT/US2023/066160 dated Jul. 14, 2023.

* cited by examiner

OSTOMY APPLIANCE WITH CUSTOMIZABLE BARRIER RING FOR LOCALIZED CONVEX SUPPORT

This is a National Stage Application of International Patent Application No. PCT/US2023/066162, filed Apr. 25, 2023, which claims the benefit of and priority to U.S. Provisional Application No. 63/403,129, filed Sep. 1, 2022, the entirety of which are incorporated fully herein by reference.

BACKGROUND

The present disclosure relates to ostomy appliances, and more particularly to a customizable convex barrier ring for use with ostomy appliances for providing localized and customized convex support around a stoma.

Ostomy pouches for the collection of body waste output from a stoma are well known and used by individuals who have had surgery such as a colostomy, ileostomy or urostomy. Ostomy pouches are generally attached to a user via an ostomy barrier, which is configured to seal against peristomal skin surfaces and protect the peristomal surfaces from exposure to stomal effluent. However, the topography of stomas and peristomal surfaces surrounding stomas can vary among patients and providing a single ostomy appliance which can effectively seal against such different peristomal surfaces and stomas can be particularly challenging. For example, a stoma may protrude more or less, or may even be flush or recessed.

A person with an ostomy having a stoma that is flush or recessed may find that applying external support or pressure from a barrier in the peristomal region aids in directing the discharge of effluent from the stoma directly into the ostomy pouch which can prevent undesirable leakage of body waste output between the barrier and the pouch. Accordingly, the effectiveness of an adhesive seal between the ostomy barrier and the peristomal skin surface (i.e., a seal formed by the adhesive layer) may be prolonged. Thus, convex inserts and convex ostomy barriers, such as ADAPTR convex barrier rings available through the assignee of the present application, have been developed to apply pressure around such peristomal regions.

However, the convexity of a conventional convex ostomy barrier or insert is fixed and may not work efficiently for all ostomates. Thus, convex ostomy barriers and convex inserts of various convexity depths have been made available in the market. Further, an ostomate may wish to incrementally adjust the convexity of an ostomy barrier to achieve an optimal convexity for his/her topography of stoma.

Accordingly, for at least the above-noted reasons, there is a critical need in the art for a customizable ostomy appliance that can accommodate a variety of stomal features and provide a desired degree of convex support to particular localized regions around the stoma inlet/opening. There is further a desire to provide a customizable ostomy appliance that can provide varying degrees of support around the stoma inlet/opening and that can enable a user to adjust or set the amount of flexibility or rigidity to different support regions. There is further a need in the art for an ostomy appliance that can provide the necessary flexibility upon application without compromising the structural rigidity as a support when in use.

BRIEF SUMMARY

Embodiments presented herein are directed to an ostomy appliance comprising a convex ring insert member. The insert member can have a curved body-side surface, an opposing pouch-side surface defining an internal cavity and an annular curved body portion between an outside flange and an engagement portion encircling a centrally-located input opening. The engagement portion can comprise a plurality of spaced-apart flexible tabs having spaces therebetween. The internal cavity can be defined by interior surfaces of the spaced-apart flexible tabs and an interior surface of the curved body portion. The spaced-apart flexible tabs can have flexibility to bend toward the internal cavity and interior surface of the curved body portion. A backfill material can be applied into at least a portion of the internal cavity along the interior surfaces of at least some of the plurality of spaced-apart flexible tabs. The backfill material can be removable from the convex ring insert. Upon application of the backfill material, the flexibility of the at least some of the plurality of spaced-apart flexible tabs can be reduced to provide a localized rigid support segment along the engagement portion.

According to embodiments presented herein, the ostomy appliance can further comprise a ring seal covering at least a portion of the body-side surface of the convex ring insert member. The backfill material can be a soft, flexible/deformable ring comprised of a biocompatible hydrocolloid material which can be pressed into the internal cavity of the convex insert ring member. Upon application, the backfill material can bind around at least some of the plurality of spaced-apart flexible tabs. The backfill material can also be comprised of a tab. The flexibility of the tab can be restricted by engagement of the tab against the interior surface of the at least some of the plurality of spaced-apart flexible tabs. The convex ring insert can be comprised of a flexible polymeric material. The ring seal can be comprised of a flexible biocompatible hydrocolloid material. The ring seal can cover an exterior surface of the plurality of flexible tabs around the input opening.

According to embodiments, the plurality of spaced-apart flexible tabs can comprise twelve tabs that encircle the entirety of the engagement portion and the input opening. Each of the twelve tabs can be substantially equivalent in size and being spaced a same distance apart from one another. The ostomy appliance can further comprise an ostomy skin barrier removably affixable to a user. The convex ring insert member can be a layer of the ostomy skin barrier. The localized rigid support segment can be adjustable by removal of the backfill material from the convex ring insert member and reapplication of the backfill material to at least a second portion of the internal cavity along the interior surfaces to from a new localized rigid support segment. Application of the backfill material into at least a second portion of the internal cavity along the interior surfaces of at least some of the plurality of spaced-apart flexible tabs can provide a second localized rigid support segment along the engagement portion. The second localized rigid support segment can be spaced apart from the localized rigid support segment.

Embodiments presented herein are further directed to a method of providing localized rigid support to a convex ring insert member of an ostomy appliance. The method can comprise providing a convex ring insert member having a curved body-side surface and an opposing pouch-side surface defining an internal cavity. The ring insert member can have an annular curved body portion between an outside flange and an engagement portion which encircles a centrally-located input opening. The engagement portion can comprise a plurality of spaced-apart flexible tabs having spaces therebetween. The internal cavity can be defined by interior surfaces of the spaced-apart flexible tabs and an interior surface of the curved body portion. The spaced-apart flexible tabs can have flexibility to bend toward the internal cavity and interior surface of the curved body portion. The method can further comprise applying a backfill material into at least a portion of the internal cavity along the interior surfaces of at least some of the plurality of spaced-apart flexible tabs. The backfill material can be removable from the convex ring insert. The method can further comprise reducing the flexibility of the at least some of the plurality of spaced-apart flexible tabs to provide a localized rigid support segment along the engagement portion.

According to embodiments, the backfill material can be a soft, flexible/deformable ring comprised of a biocompatible hydrocolloid material which can be pressed into the internal cavity of the convex insert ring member and the method can further comprise binding the backfill material around the at least some of the plurality of spaced-apart flexible tabs and covering at least a portion of the body-side surface of the convex ring insert member with a ring seal.

Embodiments presented herein are further directed to a convex ring insert member for an ostomy appliance. The convex ring insert can comprise a curved body-side surface, an opposing pouch-side surface defining an internal cavity and an annular curved body portion between an outside flange and an engagement portion encircling a centrally-located input opening. A plurality of spaced-apart flexible tabs can be provided along the engagement portion. The plurality of spaced-apart flexible tabs can have spaces therebetween and have flexibility to bend toward the internal cavity and interior surface of the curved body portion. The internal cavity can be defined by interior surfaces of the spaced-apart flexible tabs and an interior surface of the curved body portion. At least a portion of the internal cavity along the interior surfaces of at least some of the plurality of spaced-apart flexible tabs can be configured to receive a backfill material therein. The backfill material can be removable from the convex ring insert. Upon application of the backfill material, the flexibility of at least some of the plurality of spaced-apart flexible tabs can be reduced to provide a localized rigid support segment along the engagement portion.

According to embodiments, the convex ring insert member can further comprise a ring seal covering at least a portion of the body-side surface and the backfill material. The backfill material can be a soft, flexible/deformable ring comprised of a biocompatible hydrocolloid material which can be pressed into the internal cavity of the convex insert ring member and suitable for binding around at least some of the plurality of spaced-apart flexible tabs. The convex ring insert member can be comprised of a flexible polymeric material. The plurality of spaced-apart flexible tabs can encircle the entirety of the engagement portion and the input opening. Each of the tabs can be substantially equivalent in size and be spaced a same distance apart from one another. The localized rigid support segment can be adjustable by removal of the backfill material from the convex ring insert member and reapplication of the backfill material to at least a second portion of the internal cavity along the interior surfaces to form a new localized rigid support segment.

Other objects, advantages and features of the present disclosure will be understood and appreciated by persons of ordinary skill in the art from consideration of the following specification taken in conjunction with the accompanying drawings.

DETAILED DESCRIPTION

Figure 1:
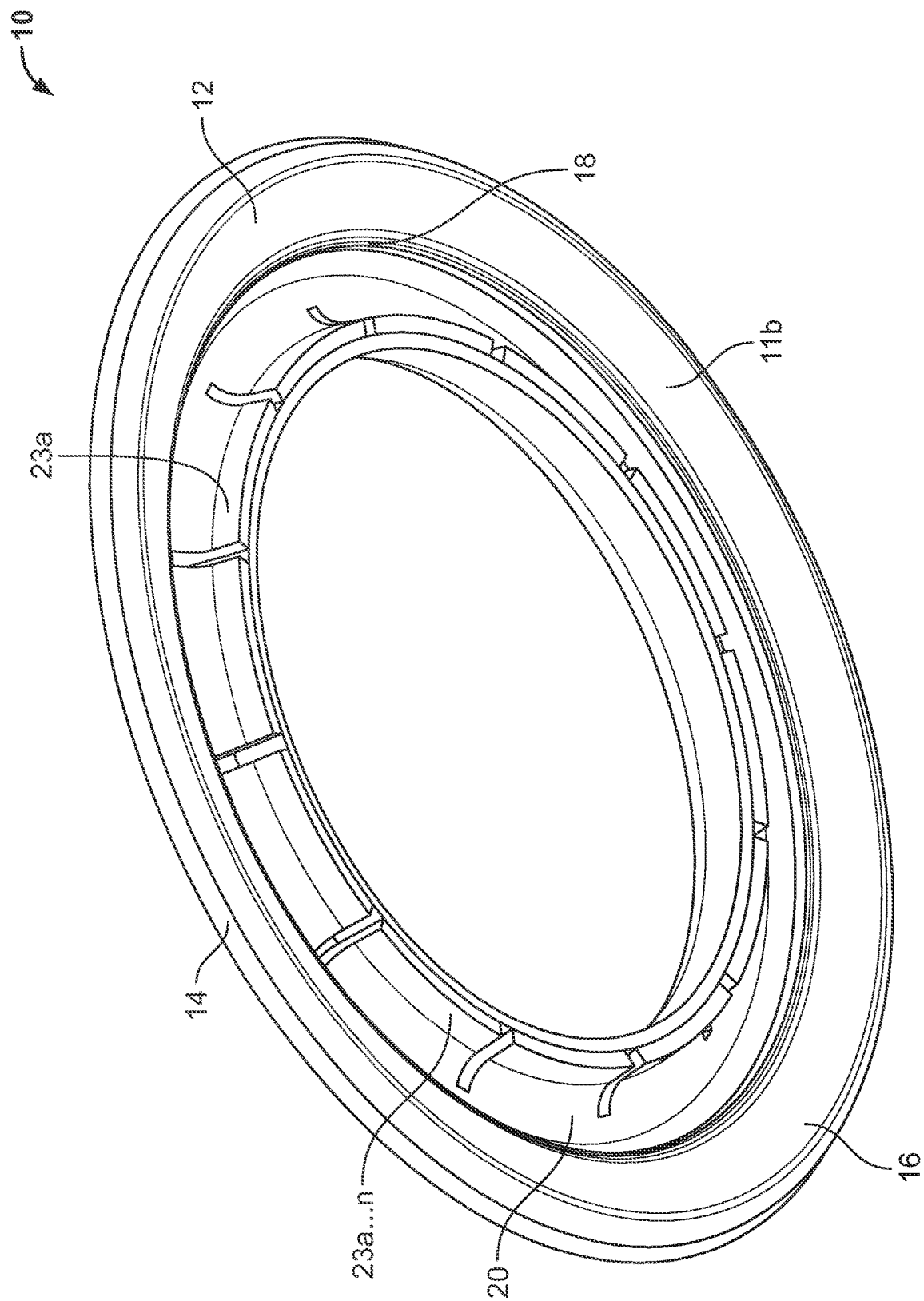
FIG. 1 is a pouch-side perspective view of a customizable barrier ring for an ostomy appliance according to embodiments presented herein.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Figure 2:
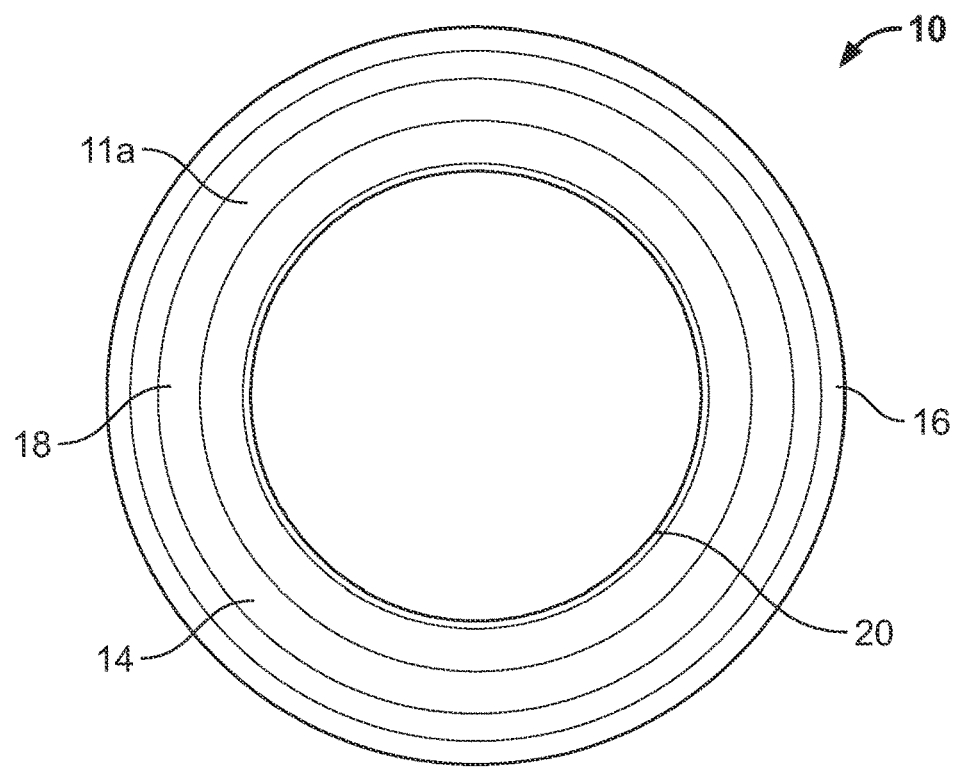
FIG. 2 is a body-side plan view of a customizable barrier ring for an ostomy appliance according to embodiments presented herein.
Figure 3:
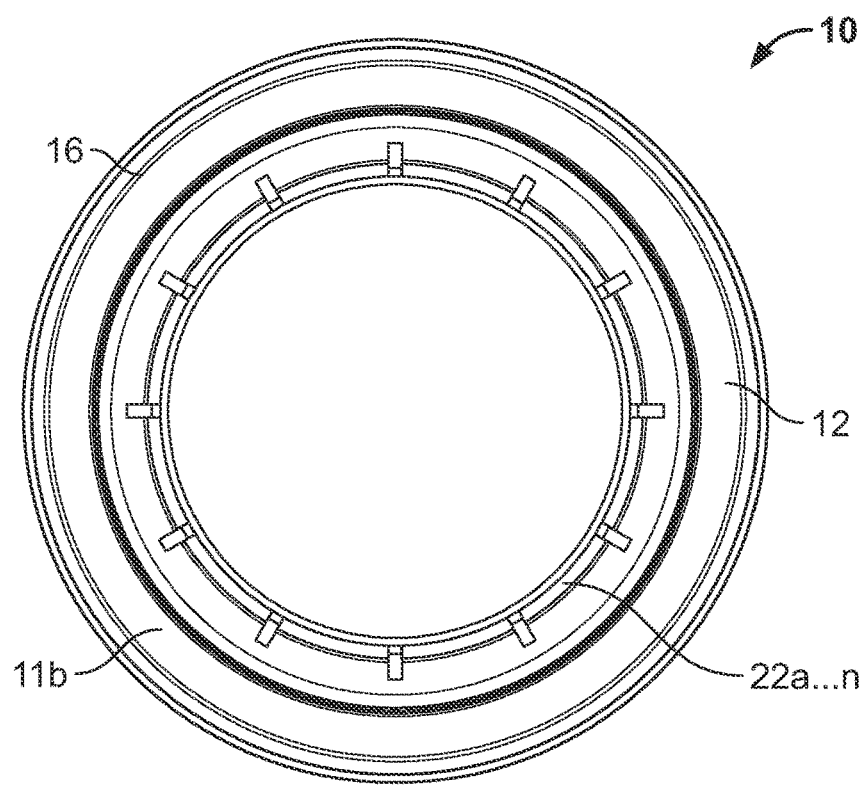
FIG. 3 is a pouch-side plan view of a customizable barrier ring for an ostomy appliance according to embodiments presented herein.

Referring now to the accompanying figures, and FIGS. 1-3 in particular, a customizable barrier ring 10 for an ostomy appliance is shown according to embodiments. As shown schematically in FIGS. 1-3, customizable barrier ring 10 can have a ring insert member 12 and a ring seal 14. The ring insert member 12 can have an outer flange 16, a middle body portion 18 and an interior stoma engagement portion 20 comprising a plurality of spaced apart flexible tabs 22a . . . n arranged around an inlet opening configured for receiving at least a portion of a stoma. Customizable barrier ring 10 can comprise an outwardly curving convex body-side surface 11a and an opposing ostomy pouch-side surface 11b. According to embodiments, customizable barrier ring 10 can be securable to, or integrated within, an ostomy appliance such as a skin barrier (not shown) with the curved body side surface 11a configured to protrude axially toward a body-side direction to provide a convex ring-like shaped body configured to apply pressure around the peristomal area. More particularly, customizable barrier ring 10 can be incorporated into and made part of an ostomy barrier which can in turn be removably coupled or secured to an ostomy pouch (not shown). Alternatively, the pouch-side surface 11b of customizable barrier ring 10 can be removably securable to a ostomy skin barrier.

As shown schematically in FIGS. 1-3, middle body portion 18 of ring insert member 12 can be between outer flange 16 and engagement portion 20 and can have a curved or elevated contour to provide depth to ring insert member 12. According to embodiments ring insert member 12 including outer flange 16, middle body portion 18 and engagement portion 20 can be comprised of a flexible biocompatible material such as silicone or other polymeric materials which can allow ring insert member 12 to bend or flex. Such flexibility can be important upon application of the customizable barrier ring 10 to the user as well as from the perspective of providing flexibly for supporting the peristomal region. As shown in FIGS. 1-3, customizable barrier ring 10 including ring insert member 12 can have an annular configuration with a round outer edge. It will be understood however that alternate shapes and configurations can be provided or utilized without limitation.

Figure 4:
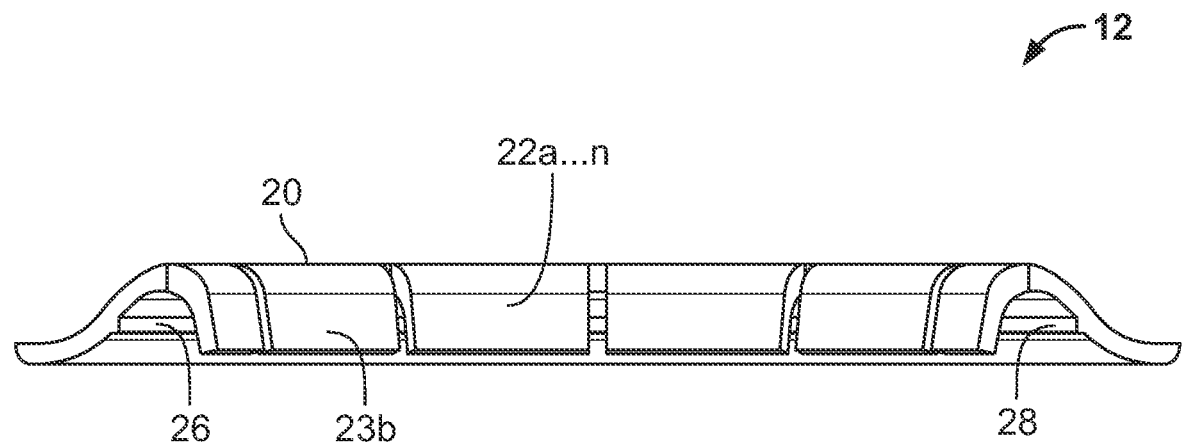
FIG. 4 is a partial cut-away elevational view of a ring insert member for an ostomy appliance according to embodiments presented herein.

According to embodiments shown in FIGS. 1, 3 and 4, a ring seal 14 can be applied over the body-side surface of ring insert member 12 and can form the body-side surface of customizable barrier ring 10. According to embodiments, ring seal 14 can be comprised of a soft, flexible biocompatible material such as, for example, a hydrocolloid material that can attract water to prevent moisture becoming trapped between the barrier and the user's skin.

As best shown in FIGS. 1 and 3, flexible tabs 22a . . . n of ring insert member 12 can be arranged entirely around engagement portion 20. According to embodiments shown schematically, flexible tabs 22a . . . n can be curved as they extend away from middle body portion 18 and configured to define the inlet opening for receiving a stoma. Tabs 22a . . . n can have side edges and opposing interior and exterior surfaces 23a, 23b. As shown in FIG. 1 and FIGS. 3-4, tabs 22a . . . n can be spaced apart from one another with spaces or slits therebetween with the spaces being defined between the side edges of adjacent tabs.

As shown schematically in FIGS. 1 and 4, the exterior surface 23b of tabs 22a . . . n can have a smooth surface suitable for engagement with locations of the peristomal surface. As shown in FIGS. 1 and 4, tabs 22a . . . n can have a bowed or curved shape between the proximal and distal ends. In ordinary use, it will be understood that when the customizable barrier ring 10 is being applied to a user, barrier ring 10 can press against the peristomal skin to facilitate the stoma to project outward to better direct discharge into an associated pouch. According to embodiments presented herein, the plurality of flexible tabs 22a . . . n work to create individual and localized sections capable of providing localized support to specific areas of the perisomal area.

According to embodiments shown schematically in FIGS. 1 and 4, tabs 22a . . . n can be evenly spaced one another around engagement portion 20 and can be identically sized with corresponding identically sized spaces therebetween. The length of tabs 22a . . . n can be substantially equivalent and the distance between adjacent spaces can also be substantially identical around the entirety of engagement portion 20. For example, the tabs 22a . . . n can have equal lengths and an equal distance between adjacent spaces around the entirety of engagement portion 20. In another example, the tabs 22a . . . n can have lengths and a distances between adjacent spaces around the entirety of engagement portion 20 such that there is no functional difference between the tabs.

As shown schematically in FIGS. 1, 3 and 4, ring insert member 12 can have an internal cavity 26 formed between the interior surface 23a of tabs 22a . . . n and the interior surface 28 of the middle body portion 18 of ring insert member 12. As shown schematically in FIG. 1-3, the internal cavity 26 can be circular when viewed from the pouch-side and have a parabolic or wave-shaped configuration when viewed in cross-section. It will be understood from the subject disclosure that the internal cavity 26 can have alternate shapes or sizes without limitation.

Figure 5:
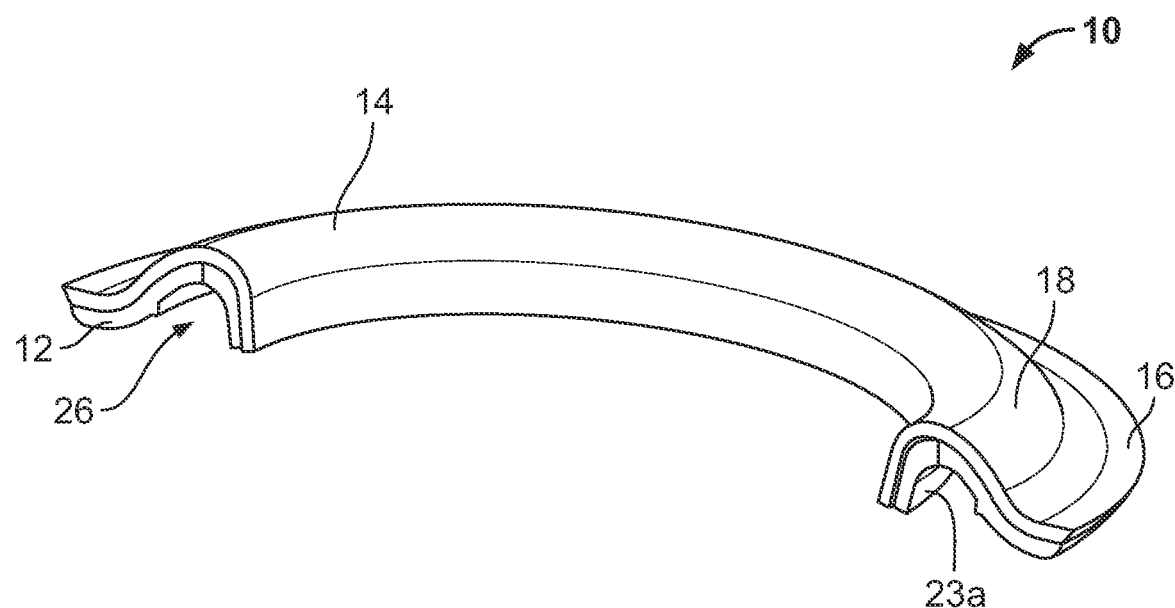
FIG. 5 is a partial cut-away body-side perspective view of a customizable barrier ring for an ostomy appliance according to embodiments presented herein.
Figure 6:
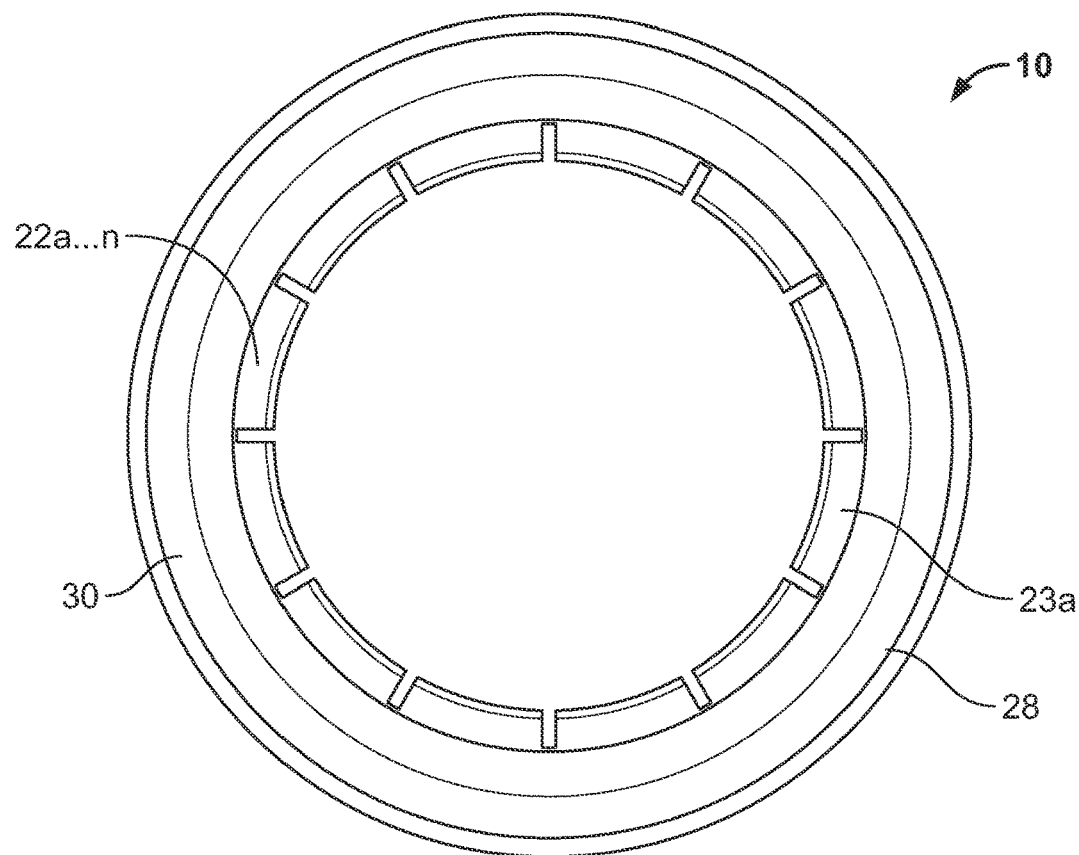
FIG. 6 is a pouch-side plan view of a ring insert member for an ostomy appliance according to embodiments presented herein.
Figure 7:
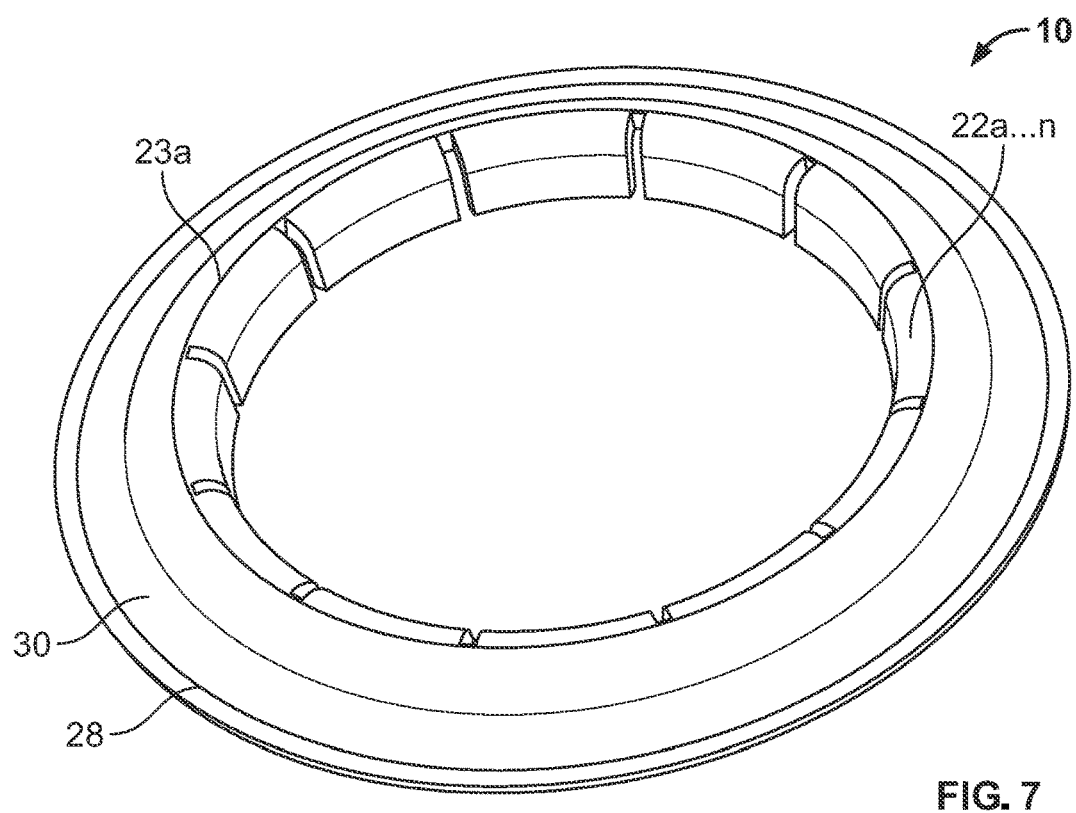
FIG. 7 is a pouch-side perspective view of a ring insert member for an ostomy appliance according to embodiments presented herein.

According to embodiments shown schematically in FIGS. 6 and 7, a backfill or binder material such as, for example, an alternative barrier mix or flexible/deformable ring member such as an Adapt™ Barrier Ring ("ABR") 30 of the type offered by Hollister Incorporated can be pressed into the internal cavity 26 of the ring insert member 12 between the interior surface of tabs 22a . . . n and the interior surface 28 of middle portion 18. The ABR can be comprised of a biocompatible hydrocolloid material which can be compressed or deformed to fit and/or fill internal cavity 26. Internal cavity 26 can be suitable for receiving and retaining the ABR along or around localized tabs 22a . . . n. More particularly, as shown schematically in FIGS. 4-5, tabs 22a-n can extend sufficiently downward to contain the ABR 30 from flowing into the input opening. A small recess 32, however, can be provided below the spaced-apart tabs 22a . . . n which can permit ABR to bind along the distal surface of the tabs 22a . . . n to improve binding or adhesion to the respective tabs 22a . . . n.

The introduction of the ABR into internal cavity 26 can work to bind particular tabs 22a . . . n along the engagement portion 20 to restrict or impede such tabs from flexing or bending. Upon employing such restriction, the bound tabs 22a . . . n can provide stiffer and more rigid convex support to localized segments of the engagement portion 20 and the associated adjacent areas of the stoma. Although FIGS. 6 and 7 illustrate entire cavity portion 16 as being filed with ABR 30, it will be recognized and appreciated that the application of ABR can be limited to specific localized tabs 22a . . . n of the engagement portion 20 and provide rigid more rigid support to only such areas, permitting the remaining tabs 22a . . . n to flex or bend in their customary manner.

Figure 8:
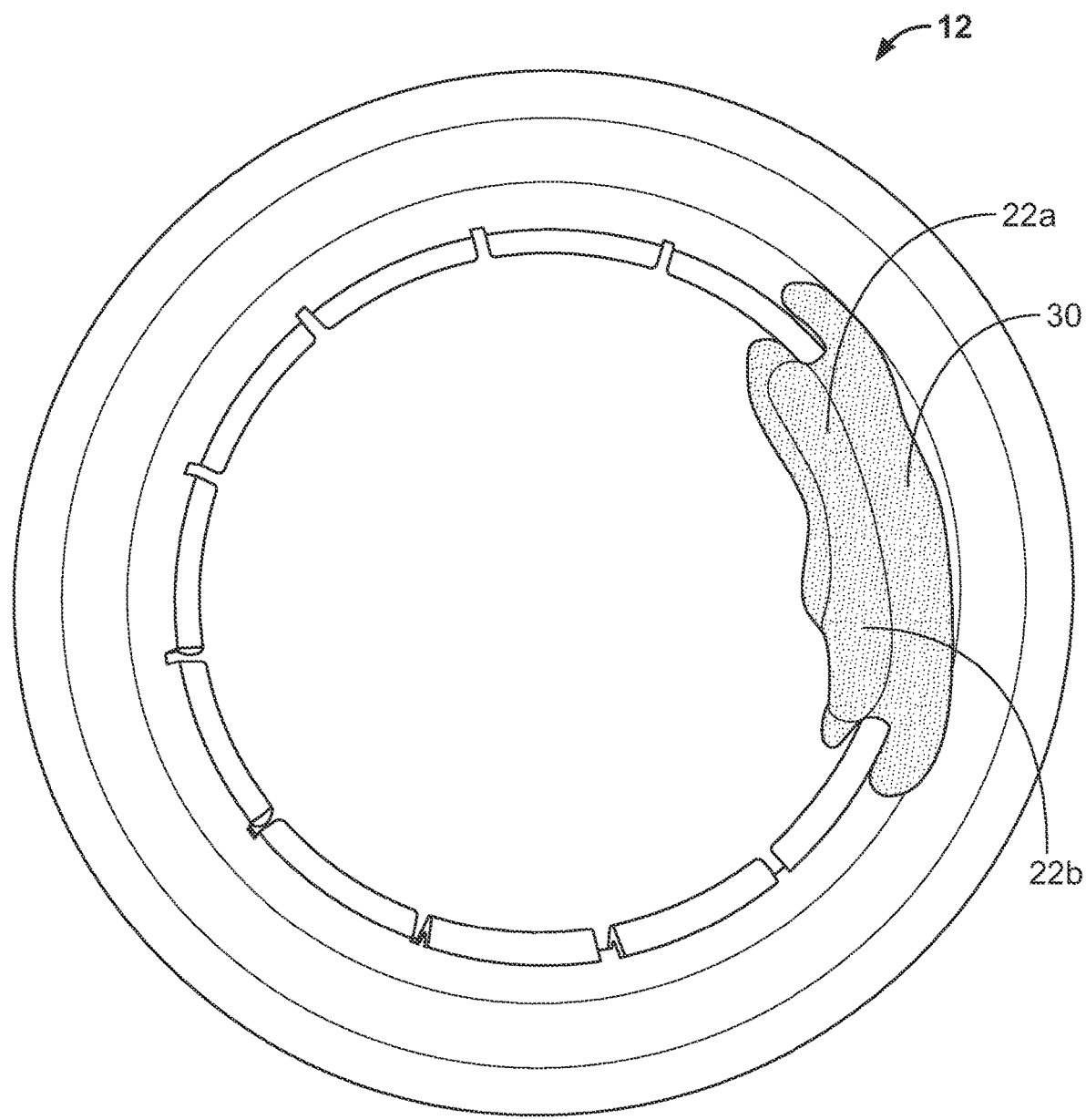
FIG. 8 is a pouch-side plan view of a ring insert member for an ostomy appliance according to embodiments presented herein.

FIG. 8 representatively illustrates a pouch-side plan view of a customizable barrier ring 10 having ABR 30 applied to only a specific localized area of the engagement portion 20 to restrict movement of tabs 22a and 22b in the location where the ABR was introduced. According to embodiments, the restriction of tabs 22a and 22b can provide a stiffer more rigid support to that area of the engagement member 20 as compared to the reminder of the tabs that were not exposed to the ABR 30. As an alternative to utilization of ABR, customizable barrier ring 10 according to embodiments presented herein can utilize a mechanical member such as an insert tab (not shown) within internal cavity 26 to physically block or restrict the spaced-apart flexible tabs 22a . . . n from bending or flexing.

According to embodiments presented herein, the customizable barrier ring 10 can be applied to a user by inserting the stoma through the inlet opening such that the ring insert member 12 encircles at least a portion of the stoma with the body side 10a of barrier ring 10 facing inward towards the user's body and pouch-side 11b is facing outward away from the user. In placing the customizable barrier ring 10 around the stoma, the soft, flexible composition of the ring insert member 10 and tabs 22a . . . n can gently push on the skin surrounding the stoma to protrude or project the stoma in the pouch-side direction to unsheathe the stoma and aid in directing the discharge of effluent from the stoma directly into the ostomy pouch.

From the subject disclosure, it will be recognized and appreciated, that customized barrier ring 10 can provide increased localized support for particular stomal locations where the adjacent stomal area requires deeper convexity or additional firmness or rigidity to be adequately supported. It will be recognized that such capabilities can provide a more customizable ostomy appliance that is adjustable to suit the particular conditions or needs of an individual user. It will be further recognized that such capabilities can reduce the need for providing, or manufacturing multiple different types of specialized ostomy appliances to attempt to suit the needs of different individuals which can be commercially impractical. Accordingly, embodiments presented herein can provide adjustable convexity to account for stomal variations between individual users and also stomal changes that may evolve over time with regard to a specific individual user who may need additional support to different areas at different times. According to embodiments presented herein, such individual can add or reduce support to particular stomal areas by modifying use and positioning of the ABR material 30. It will be appreciated that such functionality can better prevent undesirable leakage of body waste output which can improve sanitation and reduce embarrassment.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An ostomy appliance comprising:
   a convex ring insert member having a curved body-side surface and an opposing pouch-side surface defining an internal cavity, the ring insert member having an annular curved body portion between an outside flange and an engagement portion encircling a centrally-located input opening, the engagement portion comprising a plurality of spaced-apart flexible tabs having spaces therebetween, the internal cavity being defined by interior surfaces of the spaced-apart flexible tabs and an interior surface of the curved body portion, the spaced-apart flexible tabs having flexibility to bend toward the internal cavity and interior surface of the curved body portion; and
   a backfill material applied into at least a portion of the internal cavity along the interior surfaces of at least some of the plurality of spaced-apart flexible tabs, the backfill material being removable from the convex ring insert,
   wherein upon application of the backfill material, the flexibility of the at least some of the plurality of spaced-apart flexible tabs being reduced to provide a localized rigid support segment along the engagement portion.

2. The ostomy appliance of claim 1 further comprising a ring seal covering at least a portion of the body-side surface of the convex ring insert member.

3. The ostomy appliance of claim 1 wherein the backfill material is comprised of a flexible hydrocolloid material that is pressed into the internal cavity.

4. The ostomy appliance of claim 1 wherein the backfill material is a tab, the flexibility being restricted by engagement of the tab against the interior surface of the at least some of the plurality of spaced-apart flexible tabs.

5. The ostomy appliance of claim 1 wherein the convex ring insert is comprised of a flexible polymeric material.

6. The ostomy appliance of claim 2 wherein the ring seal is comprised of a flexible biocompatible hydrocolloid material.

7. The ostomy appliance of claim 2 wherein the ring seal covers an exterior surface of the plurality of flexible tabs around the input opening.

8. The ostomy appliance of claim 1 wherein the plurality of spaced-apart flexible tabs comprises twelve tabs that encircle the entirety of the engagement portion and the input opening, each of the twelve tabs being substantially equivalent in size and being spaced a same distance apart from one another.

9. The ostomy appliance of claim 1 further comprising an ostomy skin barrier removably affixable to a user, the convex ring insert member being a layer of the ostomy skin barrier.

10. The ostomy appliance of claim 1 wherein the localized rigid support segment is adjustable by removal of the backfill material from the convex ring insert member and reapplication of the backfill material to at least a second portion of the internal cavity along the interior surfaces to from a new localized rigid support segment.

11. The ostomy appliance of claim 1 further comprising application of the backfill material into at least a second portion of the internal cavity along the interior surfaces of at least some of the plurality of spaced-apart flexible tabs to provide a second localized rigid support segment along the engagement portion, the second localized rigid support segment being spaced apart from the localized rigid support segment.

12. A method of providing localized rigid support to a convex ring insert member of an ostomy appliance comprising:
   providing the convex ring insert member having a curved body-side surface and an opposing pouch-side surface defining an internal cavity, the ring insert member having an annular curved body portion between an outside flange and an engagement portion encircling a centrally-located input opening, the engagement portion comprising a plurality of spaced-apart flexible tabs having spaces therebetween, the internal cavity being defined by interior surfaces of the spaced-apart flexible tabs and an interior surface of the curved body portion, the spaced-apart flexible tabs having flexibility to bend toward the internal cavity and interior surface of the curved body portion; and
   applying a backfill material into at least a portion of the internal cavity along the interior surfaces of at least some of the plurality of spaced-apart flexible tabs, the backfill material being removable from the convex ring insert,
   reducing the flexibility of the at least some of the plurality of spaced-apart flexible tabs to provide a localized rigid support segment along the engagement portion.

13. The method of claim 12 wherein the backfill material is comprised of a flexible hydrocolloid material, the method further comprising pressing the hydrocolloid material into the internal cavity.

14. The method of claim 12 further comprising covering at least a portion of the body-side surface of the convex ring insert member with a ring seal.

15. A convex ring insert member for an ostomy appliance comprising:
   a curved body-side surface and an opposing pouch-side surface defining an internal cavity;
   an annular curved body portion between an outside flange and an engagement portion encircling a centrally-located input opening;
   a plurality of spaced-apart flexible tabs along the engagement portion, the plurality of spaced-apart flexible tabs having spaces therebetween and having flexibility to bend toward the internal cavity and interior surface of the curved body portion;

wherein the internal cavity is defined by interior surfaces of the spaced-apart flexible tabs and an interior surface of the curved body portion;

wherein at least a portion of the internal cavity along the interior surfaces of at least some of the plurality of spaced-apart flexible tabs is configured to receive a backfill material therein, the backfill material being removable from the convex ring insert, and wherein upon application of the backfill material, the flexibility of the at least some of the plurality of spaced-apart flexible tabs being reduced to provide a localized rigid support segment along the engagement portion.

16. The convex ring insert member of claim 15 further comprising a ring seal covering at least a portion of the body-side surface.

17. The convex ring insert member of claim 15 wherein the backfill material comprises a flexible hydrocolloid material.

18. The convex ring insert member of claim 15 wherein the convex ring insert member is comprised of a flexible polymeric material.

19. The convex ring insert member of claim 15 wherein the plurality of spaced-apart flexible tabs encircle the entirety of the engagement portion and the input opening, each of the tabs being substantially equivalent in size and being spaced a same distance apart from one another.

20. The convex ring insert member of claim 15 wherein the localized rigid support segment is adjustable by removal of the backfill material from the convex ring insert member and reapplication of the backfill material to at least a second portion of the internal cavity along the interior surfaces to from a new localized rigid support segment.

* * * * *